(12) United States Patent
Rajala

(10) Patent No.: US 11,313,062 B2
(45) Date of Patent: Apr. 26, 2022

(54) APPARATUS AND METHOD FOR APPLYING A FIRST WEB TO A BASE WEB IN A NONLINEAR PATTERN

(71) Applicant: Kimberly-Clark Worldwide, Inc., Neenah, WI (US)

(72) Inventor: Gregory John Rajala, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 268 days.

(21) Appl. No.: 16/334,957

(22) PCT Filed: Sep. 30, 2016

(86) PCT No.: PCT/US2016/054655
§ 371 (c)(1),
(2) Date: Mar. 20, 2019

(87) PCT Pub. No.: WO2018/063283
PCT Pub. Date: Apr. 5, 2018

(65) Prior Publication Data
US 2020/0024779 A1 Jan. 23, 2020

(51) Int. Cl.
*D04H 1/593* (2012.01)
*A61F 13/15* (2006.01)
(Continued)

(52) U.S. Cl.
CPC ....... *D04H 1/593* (2013.01); *A61F 13/15699* (2013.01); *A61F 13/15764* (2013.01);
(Continued)

(58) Field of Classification Search
CPC . B32B 37/144; B32B 37/20; A61F 13/15609; A61F 13/15764;
(Continued)

(56) References Cited

U.S. PATENT DOCUMENTS 4,915,767 A * 4/1990 Rajala ............... A61F 13/15609
156/440
7,000,260 B2 2/2006 Rajala et al.
(Continued)

FOREIGN PATENT DOCUMENTS

CN 1085494 A 4/1994
CN 102378608 A 3/2012
(Continued)

*Primary Examiner* — Linda L Gray
(74) *Attorney, Agent, or Firm* — Kimberly-Clark Worldwide, Inc.

(57) ABSTRACT

An apparatus and method for applying a first web to a base web in a nonlinear pattern as the base web is advanced in a machine direction in contact with a back-up roller are disclosed. The apparatus can include a guide roller and a guide roller translations system. The guide roller can be configured to define a nip with the back-up roller. The guide roller translation system can be configured to allow the guide roller to move with respect to the back-up roller to control the position of the nip to allow the first web to be applied to the base web in the non-linear pattern in the machine direction.

7 Claims, 10 Drawing Sheets

(51) Int. Cl.
*B32B 37/14* (2006.01)
*B32B 37/20* (2006.01)
*D04H 13/00* (2006.01)
*B65H 39/16* (2006.01)

(52) U.S. Cl.
CPC ........ *B65H 39/16* (2013.01); *A61F 13/15593* (2013.01); *A61F 2013/1591* (2013.01); *B32B 37/144* (2013.01); *B32B 37/20* (2013.01); *B65H 2801/57* (2013.01); *D04H 13/00* (2013.01); *Y10T 156/17* (2015.01)

(58) Field of Classification Search
CPC ....... A61F 13/15699; A61F 2013/1591; Y10T 156/17; D04H 13/00; D04H 17/12; D04H 1/593; D10B 2509/026; B65H 39/16; B65H 2801/57
See application file for complete search history.

(56) References Cited

U.S. PATENT DOCUMENTS

| | | |
|---|---|---|
| 8,720,518 B2 | 5/2014 | Rajala |
| 9,095,474 B2 | 8/2015 | Nakano et al. |
| 9,271,878 B2 | 3/2016 | Nakano et al. |
| 9,283,120 B2 | 3/2016 | Fort |
| 2002/0023706 A1 | 2/2002 | Vogt et al. |
| 2004/0123954 A1 | 7/2004 | Yoneoka et al. |
| 2007/0142799 A1 | 6/2007 | Ales et al. |
| 2008/0316454 A1 | 12/2008 | Opower et al. |
| 2012/0152440 A1 | 6/2012 | Malchow et al. |
| 2012/0216973 A1 | 8/2012 | Ales et al. |
| 2012/0283681 A1 | 11/2012 | Lohoff |
| 2015/0346834 A1 | 12/2015 | Martinez Fernandez et al. |

FOREIGN PATENT DOCUMENTS

| | | |
|---|---|---|
| DE | 102005038430 A1 | 2/2007 |
| JP | 2006141642 A | 6/2006 |
| WO | 11004605 A1 | 1/2011 |
| WO | 13068451 A1 | 5/2013 |

\* cited by examiner

APPARATUS AND METHOD FOR APPLYING A FIRST WEB TO A BASE WEB IN A NONLINEAR PATTERN

BACKGROUND

The present invention relates generally to an apparatus for and methods of applying a first web to a base web, and more particularly, to an apparatus for and a method of adhesively bonding a first web in a nonlinear pattern to a moving base web.

Absorbent articles, such as disposable diapers, training pants, adult incontinence articles and the like, generally include several different components that are bonded together. Typical absorbent articles include a bodyside liner, an outer cover, and an absorbent core disposed between the liner and outer cover. Besides the liner, the outer cover, and the absorbent core, typical absorbent articles also include a number of discrete components, e.g., fasteners, waist elastics, leg elastics. These discrete components of the article are often bonded to the bodyside liner and/or the outer cover. For example, it is known to adhesively bond leg elastics in a curved pattern to a continuous web of outer cover material or bodyside liner material.

Known techniques for bonding leg elastics to a web moving at high line speeds are often limited in the amount of displacement (e.g., the amount of amplitude in a curved pattern) that can be achieved. Thus, leg elastics in known absorbent articles produced at high line speeds are often straight or relatively straight. The leakage protection and the aesthetic appearance of known absorbent articles can be improved, however, by incorporating leg elastics with significant curvature along their lengths.

Efforts to place leg elastics with significant amounts of displacement (i.e., curvature) onto a web at high line speeds have either been unsuccessful and/or face manufacturing reliability issues that affect machine run efficiency. Challenges with these known techniques are exacerbated as machine line speeds increase. These efforts have resulted in leg elastics being placed off target. Moreover, the deviation of the applied leg elastics from the target was not always the same. Some manufacturing issues, such as an elastic web breaking, cause the machine to be shut down, and thus, negatively impact machine line efficiency.

As a result, it is desirable to provide an apparatus for and method of applying a first web in a nonlinear manner to a base web that can provide greater capabilities in providing a wider amplitude in a pattern of the first web to a base web and/or at greater machine line speeds. It is also desirable to provide an apparatus for and method of applying a first web in a nonlinear manner to a base web that provides the desired pattern with more reliability and operates under more favorable conditions for the first web.

SUMMARY

In one aspect, an apparatus for applying a first web to a base web in a nonlinear pattern as the base web is advanced in a machine direction in contact with a back-up roller is provided. The apparatus can include a guide roller and a guide roller translation system. The guide roller can be configured to define a nip with the back-up roller. The guide roller translation system can be configured to allow the guide roller to move with respect to the back-up roller to control the position of the nip to allow the first web to be applied to the base web in the non-linear pattern in the machine direction.

In another aspect, a method for applying a first web to a base web in a nonlinear pattern is provided. The method can include providing the first web and providing the base web. The method can also include advancing the base web in a machine direction and advancing the first web in the machine direction. The method can also include providing a nip for applying the first web and the base web. The nip can be defined by a back-up roller and a guide roller. The first web can be engaged by the guide roller. The method can additionally include controlling a cross direction position of the first web in relation to the base web by adjusting a position of the guide roller with respect to the back-up roller to allow the first web to be applied to the base web in the non-linear pattern in the machine direction.

DETAILED DESCRIPTION

Figure 1:
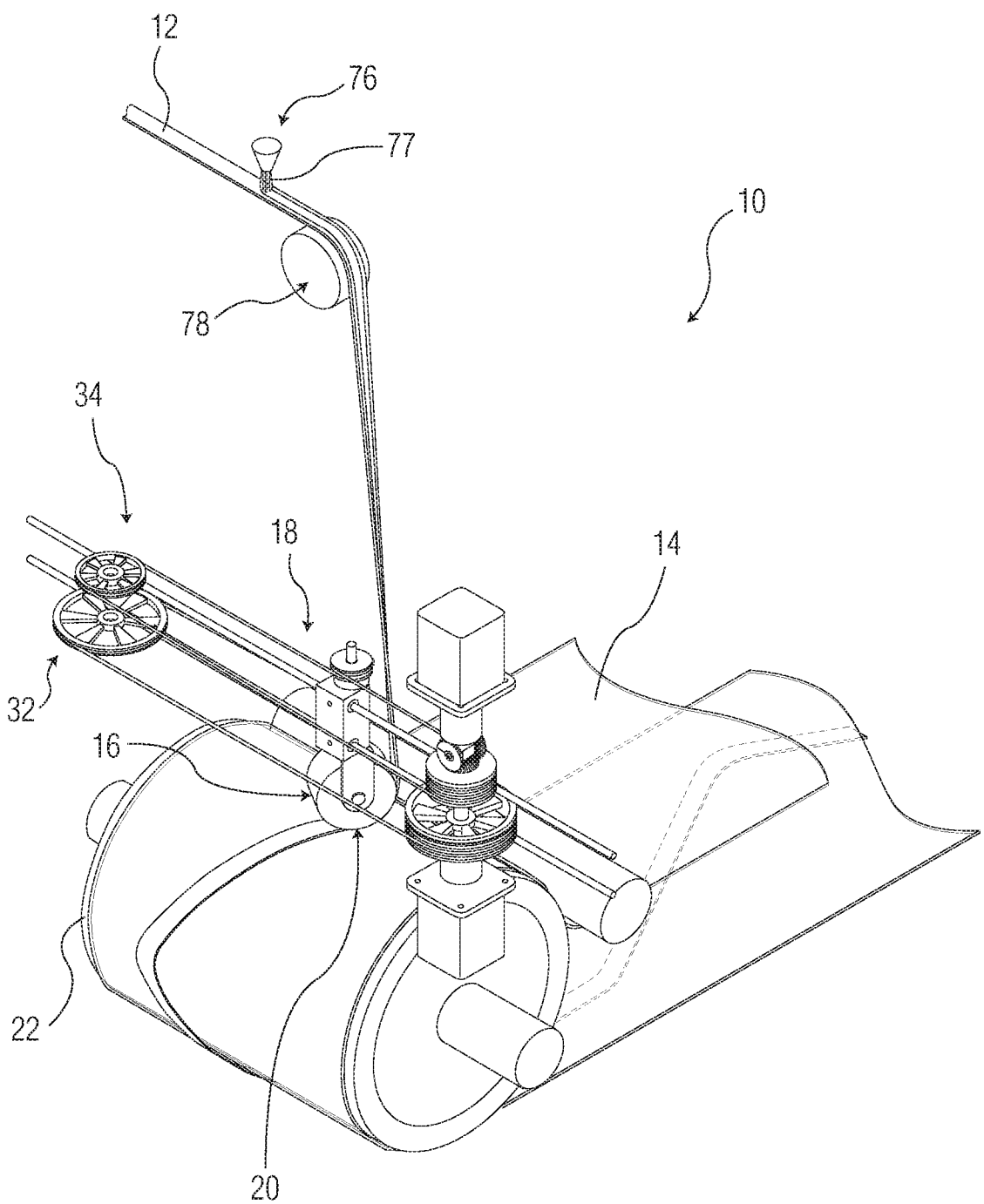
FIG. 1 illustrates a top, front perspective view of an exemplary embodiment of an apparatus for applying a first web to a base web in a nonlinear pattern.
Figure 2:
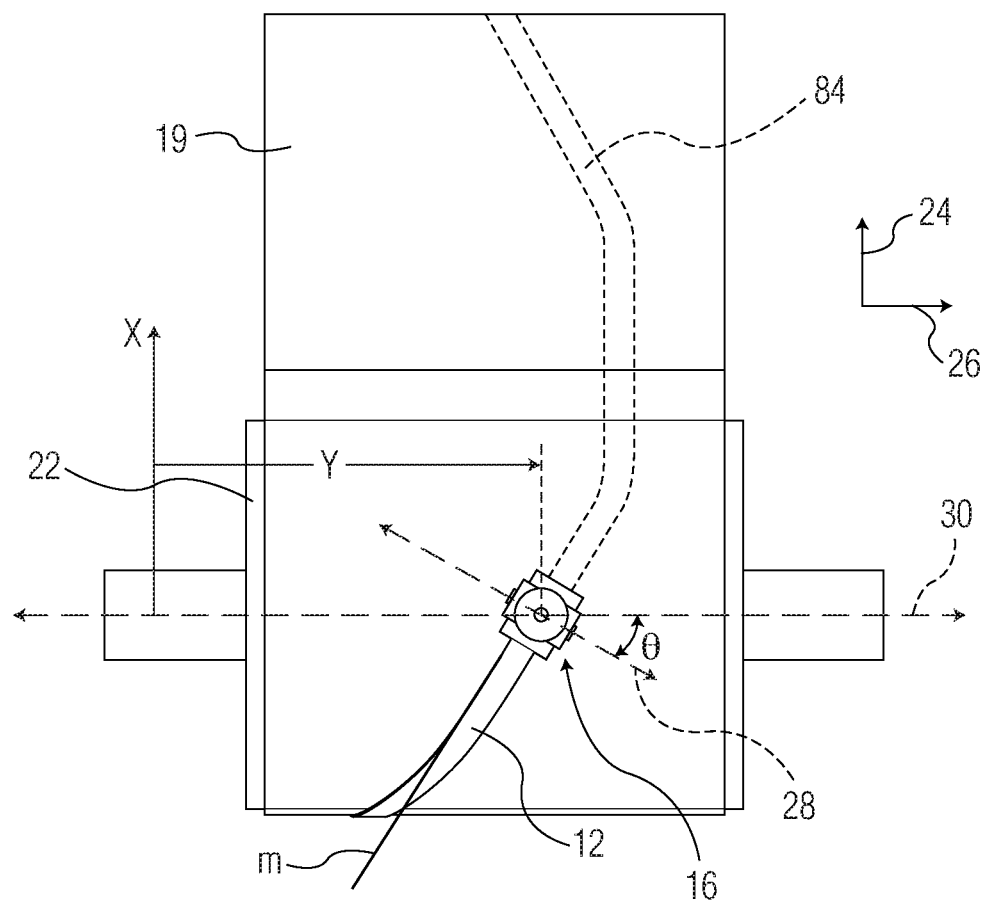
FIG. 2 illustrates a top plan view of the embodiment displayed in FIG. 1.

Referring to FIGS. 1 and 2, an apparatus 10 for guiding and applying a first web 12 onto a base web 14 in a nonlinear pattern 84 is illustrated. The apparatus 10 can include a guide roller 16 and a guide roller translation system 18. The guide roller 16 can be configured to define a nip 20 with a back-up roller 22 and can be configured to move with respect to the back-up roller 22 to control the position of the nip 20 to allow the first web 12 to be applied to the base web 14 in the nonlinear pattern 84 in the machine direction 24. As illustrated in FIG. 2, the machine direction 24 is the direction the base web 14 is generally advanced, and is perpendicular to the cross machine direction 26. The guide roller translation system 18 can support the guide roller 16 and can be configured to allow the guide roller 16 to move with respect to the back-up roller 22 to control the position of the nip 20 to allow the first web 12 to be applied to the base web 14 in the non-linear pattern 84 in the machine direction 24.

FIG. 2 illustrates a top plan view of the guide roller 16, with portions of the guide roller translation system 18 being removed for clarity. As illustrated in FIG. 2, the guide roller 16 includes a guide roller rotational axis 28. The back-up roller 22 includes a back-up roller rotational axis 30. As will be explained in further detail below, the apparatus 10 is configured such that the guide roller 16 can be configured to move with respect to the back-up roller 22 in a cross-direction 26. The apparatus 10 can also be configured such that the guide roller 16 can be configured to move with respect to the back-up roller 22 via the guide roller 16 pivoting with respect to the back-up roller 22. In other words, the guide roller 16 can pivot with respect to the back-up roller 22 such that the guide roller rotational axis 28 defines a lead angle θ with respect to the back-up roller rotational axis 30.

Figure 3:
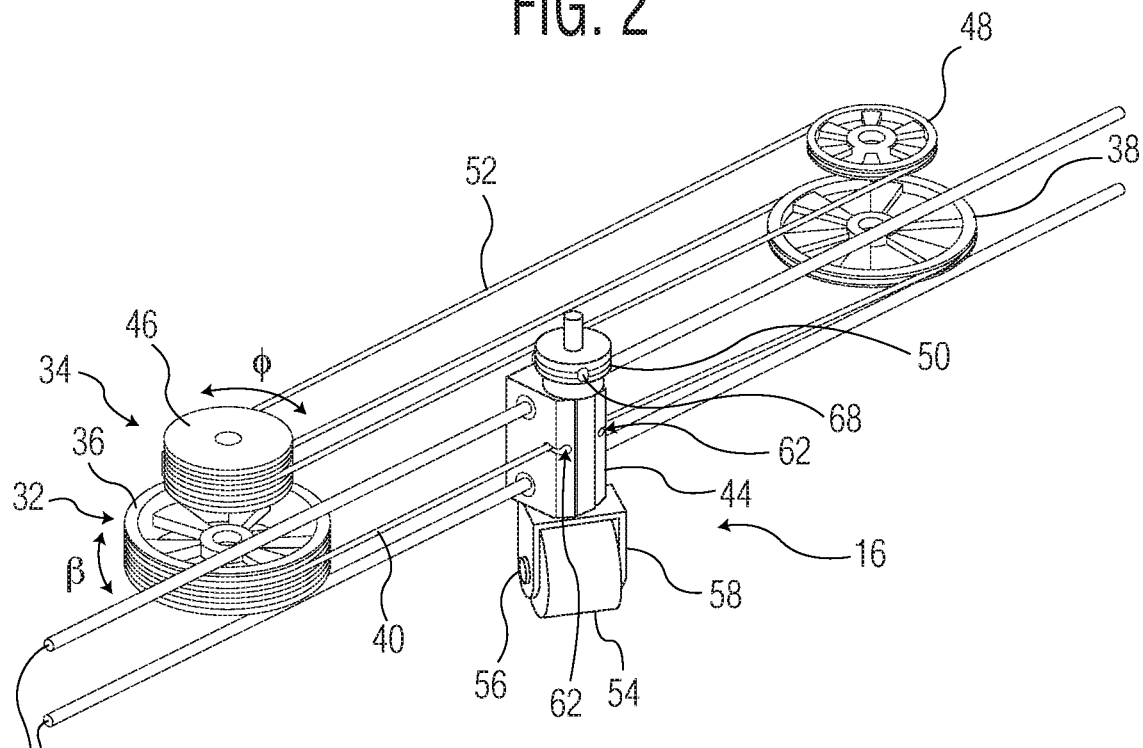
FIG. 3 illustrates a top, rear perspective view of the guide translation system of the embodiment displayed in FIG. 1.

Referring to FIGS. 1 and 3, in one embodiment, the guide roller translation system 18 can include components configured to allow the guide roller 16 to move cross directionally with respect to the back-up roller 22 and to pivot with respect to the back-up roller 22, as noted above. In one embodiment, the guide roller translation system 18 can include a cross direction funicular mechanism 32 and an angular funicular mechanism 34. As illustrated in FIG. 3, the cross direction funicular mechanism 32 of the guide translation system 18 can include a cross direction windlass 36, a cross direction pulley 38, a cross direction cable 40, at least one guide rod 42, and a guide block 44. Preferably, the guide roller translation system 18 includes two guide rods 42. The cross direction cable 40 is configured to be wound and unwound on the cross direction windlass 36 and the cross direction pulley 38. The guide rods 42 can be mounted to surrounding support structure (not shown for clarity) such that the guide rods 42 are substantially parallel to the cross direction 26, as shown in FIG. 1. Support structure can include known machine framework and/or support bracketry, such as a back plate for a respective machine line. As will be explained in more detail below, the guide block 40 can be slidably mounted to the guide rods 42 and mounted to the cross direction cable 40, such that the guide block 40 can move in the cross direction 26.

As depicted in FIG. 3, the angular funicular mechanism 34 of the guide roller translation system 18 can include an angular windlass 46, an angular pulley 48, a guide windlass 50, and an angular cable 52. The angular cable 52 can be configured to be wound and unwound on the angular windlass 46, the angular pulley 48, and the guide windlass 50. As illustrated in the embodiment in FIG. 3 and also illustrated in FIG. 5, the guide roller 16 can include a roller 54 mounted on a shaft 56 and that can revolve about the shaft 56. The shaft 56 can be mounted to a bracket 58. The bracket 58 can be mounted to the guide block 44 such that the bracket 58 can swivel with respect to the guide block 44. As the bracket 58 swivels with respect to the guide block 44, the guide roller rotational axis 28 can define the lead angle θ with respect to the back-up roller rotational axis 30, as described above and as illustrated in FIG. 2.

Figure 4:
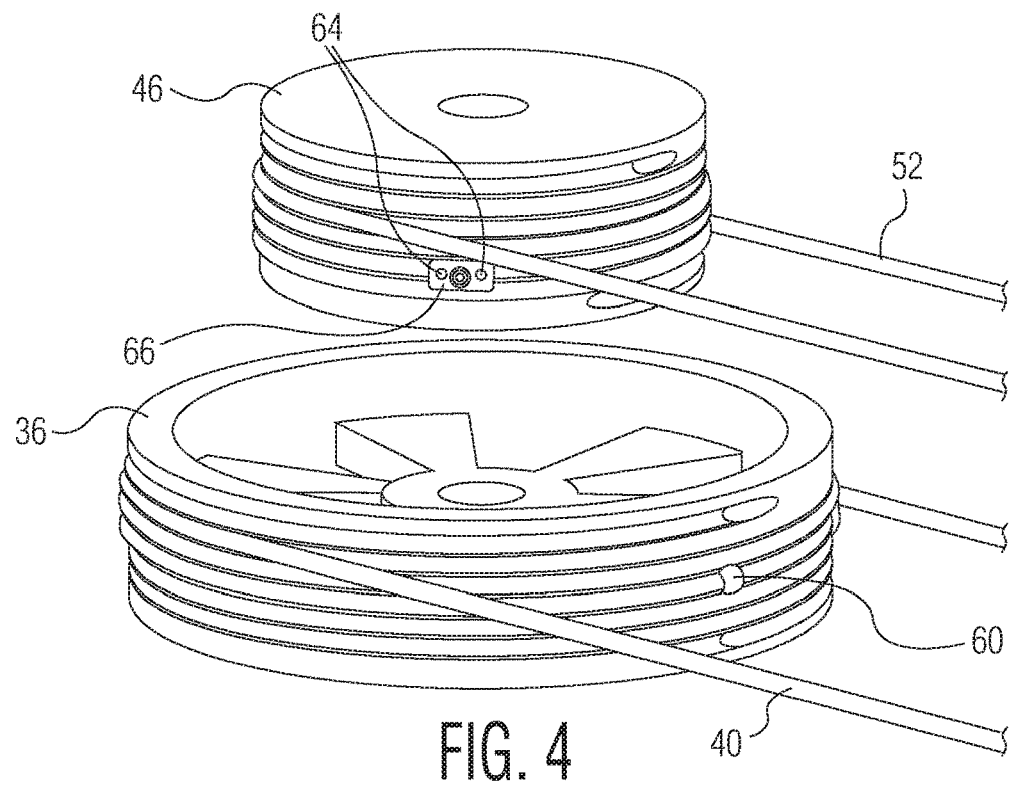
FIG. 4 illustrates a detailed perspective view of the cross direction windlass and the angular windlass of the guide translation system displayed in FIG. 3.

FIG. 4 illustrates further detail of the cross direction windlass 36 and the cross direction cable 40. A ball 60 can be fixedly coupled to a section of the cross direction cable 40 and can sit in a detent (not shown) in the cross direction windlass 36. Preferably, the ball 60 is fixedly coupled to the midsection of the cross direction cable 40. The ball 60 can be held in place by the tension of cross direction cable 40. The cross direction cable 40 can be wound or unwound from the cross direction windlass 36 and the cross direction pulley 38, and the ball 60 and the detent combined with the friction of the cross direction cable 40 and the cross direction windlass 36 keeps the cross direction cable 40 from slipping on the cross direction windlass 36 to maintain a steady relationship between the cross direction windlass rotation angle ß (labeled in FIG. 12) and a cross direction cable 40 end position. Each free end of the cross direction cable 40 can be secured to the guide block 44, as depicted in FIG. 3. As an example, a ball (not shown) could be fastened to each free end of the cross direction cable 40 and can be secured in apertures 62 in the guide block 44. The cross direction pulley 38 can be adjusted in a cross direction 26 to remove any slack in the cross direction cable 40 to reduce potential for backlash in the cross direction cable 40 between the cross direction windlass 36 and the guide block 44. In one example, cross direction pulley 38 could be mounted on a slide mechanism (not shown) that includes a jacking screw that could move the cross direction pulley 38 in the cross direction 26 to take up slack in the cross direction cable 40 and that could be locked to maintain tension in the cross direction cable 40.

Figure 5:
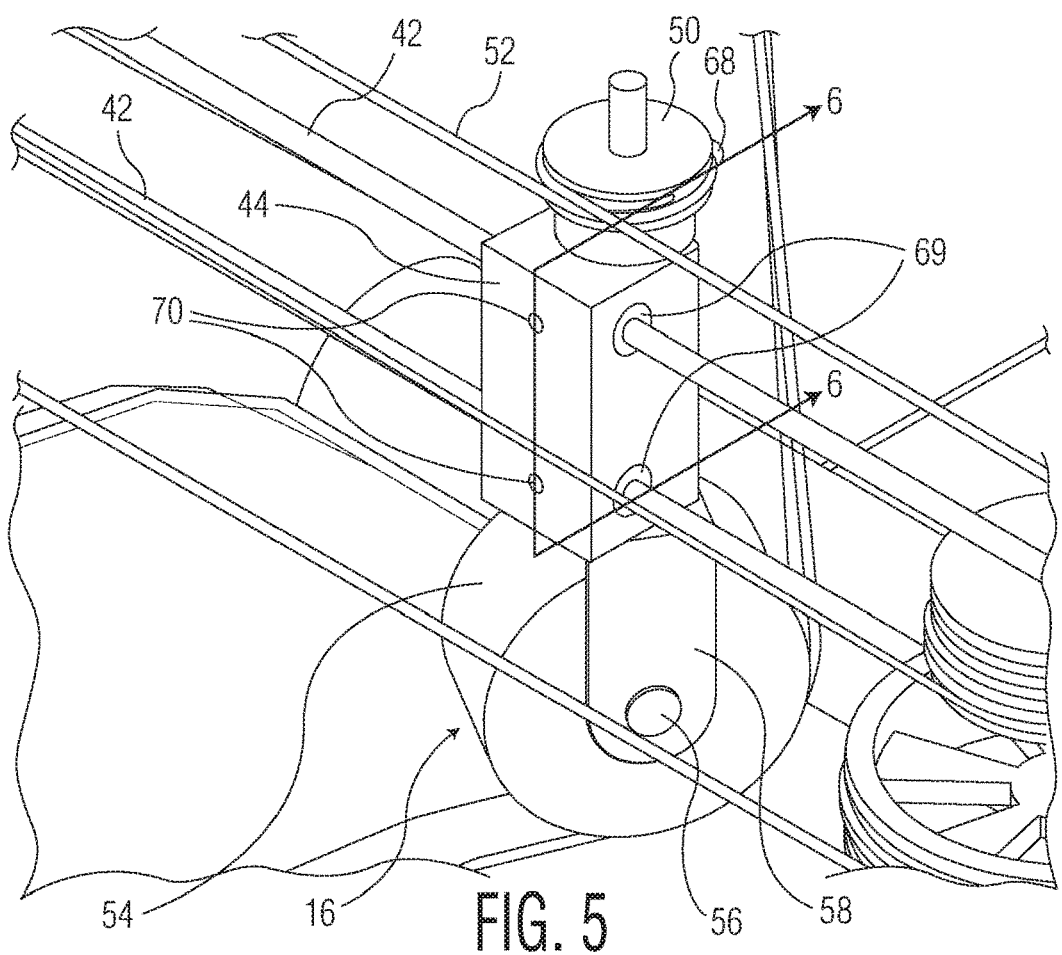
FIG. 5 illustrates a detailed perspective view of select components of the guide translation system displayed in FIG. 3, including the guide windlass, guide block, guide rods, and guide roller.

FIG. 4 also illustrates further detail of the angular windlass 46 and the angular cable 52. The angular cable 52 can be fastened to the angular windlass 46 and can be wound and unwound from the angular windlass 46. In the illustrated embodiment, a ball 64 can be coupled to each free end of the angular cable 52, and similar to the ball 60 for the cross direction cable 40 discussed above, the balls 64 can sit in detents (not pictured) in the angular windlass 46 and can be held in place with a retainer plate 66. Referring back to FIG. 3 (and as also illustrated in FIG. 5), a third ball 68 for the angular funicular mechanism 34 can be fixedly coupled to a section of the angular cable 52. Preferably, the third ball 68 is fixedly coupled to the midsection of the angular cable 52. The third ball 68 can be held in a fixed position on the guide windlass 50 by sitting in a detent (not shown) on the guide windlass 50. The balls 64, 68 and detents combined with the friction of the angular cable 52 on each of the angular windlass 46 and the guide windlass 50 keep the angular cable 52 from slipping and to maintain a steady relationship between the angular windlass angle φ (see FIG. 12), lead angle θ, and the cross directional position Y of the guide roller 16 (see FIG. 2). The angular pulley 48 can be adjusted in a cross direction 26 to remove any slack in the angular cable 52 to reduce potential for backlash in the angular cable 52 between the angular windlass 46 and the guide windlass 50. In one example, angular pulley 48 could be mounted on a slide mechanism (not shown) that includes a jacking screw that could move the angular pulley 48 in the cross direction 26 to take up slack in the angular cable 52 and that could be locked to maintain tension in the angular cable 52.

Figure 6:
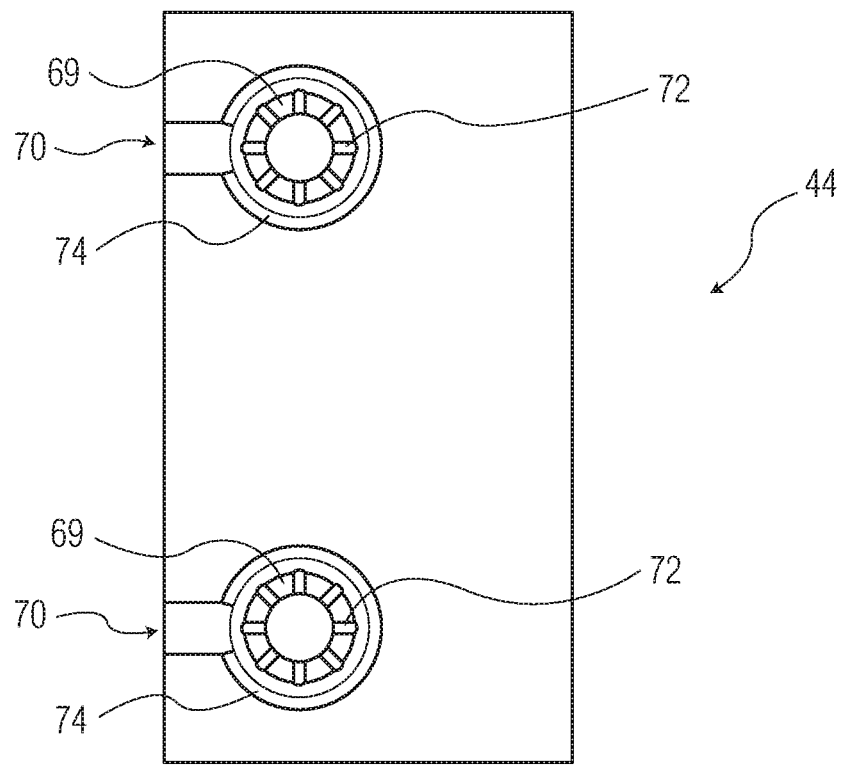
FIG. 6 illustrates a cross-sectional view of the guide block taken along line 6-6 in FIG. 5.

As illustrated in the detailed view of FIG. 5, the guide block 44 can be slidably mounted to the guide rods 42. The guide rods 42 can be received in bushings 69 mounted in the guide block 44. In a preferred embodiment, the bushings 69 can be provided with pneumatic ports 70. As depicted in the cross-sectional view of FIG. 6, the pneumatic ports 70 can receive pressurized air and transfer the pressurized air to a plurality of bushing ports 72 (only one bushing port 72 being labeled on each bushing 69 for clarity) through a surround port 74 to create an air bearing to reduce metal to metal contact between the guide rods 42 and the guide block 44. Such an air bearing has advantages over plain bushings and ball bearings when operating at high line speeds in which the guide block 44 may move along the guide rods 42 at high velocities.

The roller 54 of the guide roller 16 can rotate in the opposite direction of the back-up roller 22 in forming the nip 20. The back-up roller 22 can be driven (i.e., rotated) by suitable drive means, such as, for example, electric motors (not shown). As a result, the rotational speed of the roller 54 and the back-up roller 22 (as measured at the rolls' outer surface) can be the same or can differ. That is, the rollers 54, 22 can operate at the same or different rotational speeds.

Each of the rollers 54, 22 in the illustrated embodiment is cylindrical with a smooth outer surface. It is contemplated, however, that one or both of the rollers 54, 22 can have shapes other than cylindrical and that the outer surface may be other than smooth (i.e., patterned). In addition, the rollers 54, 22 can be formed from any suitable, durable material, such as, for example, hardened metal or steel, hardened rubber, resin-treated cotton, or polyurethane. The rollers 54, 22 can be formed from the same material or different materials. In the illustrated embodiment, for example, the roller 54 can be a steel roll covered with silicone rubber having a 55 A to 70 A Shore Durometer to facilitate release of any adhesive that may contact the roller 54, and the back-up roller 22 can be a hardened steel roll.

The temperature of the outer surface of at least one of the rollers 54, 22 can be controlled to heat or cool the respective roll. In one suitable embodiment, the outer surface of at least one of the rollers 54, 22 is cooled to inhibit adhesive from bonding to or otherwise adhering to the outer surface of the roller. In another suitable embodiment, the outer surface of at least one of the rollers 54, 22 is heated to enhance bonding between first web 12 and the base web 14.

Referring back to FIG. 1, the apparatus 10 can also comprise an adhesive unit 76 for applying adhesive 77 to at least one of the first web 12 and the base web 14 prior to the first web 12 and the base web 14 entering the nip 20. In one embodiment, the adhesive unit 76 can be configured such that the adhesive 77 can be applied to the first web 12, such as demonstrated in the embodiment depicted in FIG. 1. It is understood that any suitable adhesive unit 76 can be used to apply the adhesive 77 to the first web 12 and/or the base web 14. Although it is shown that the adhesive unit 76 can apply adhesive 77 to the first web 12, it is contemplated, however, that adhesive 77 can be applied to the base web 14 instead of, or in addition to, the first web 12. The adhesive 77 can be heated to a suitable temperature and driven to the adhesive unit 76 at a suitable pressure by an adhesive source. The adhesive 77 can bond the first web 12 to the base web 14 by the force provided by the nip 20.

The first web 12 can be formed from any suitable material including, but not limited to, wovens, nonwovens, films, foams, or combinations thereof. The material can be stretchable, non-stretchable, elastic or inelastic. In a preferred embodiment, the first web 12 can be elastic. In one suitable embodiment, the first web 12 can be an elastomeric material suitable for use as leg elastics in absorbent articles. The first web 12 can be an elastomeric laminate comprising one or more elastic materials (such as LYCRA strands). The first web 12 can be a single sheet of elastic material, an elastomeric laminate that is folded to sandwich one or more elastic materials, or an elastomeric laminate including two separate webs that have one or more elastomeric materials sandwiched therebetween. It is also contemplated that one of the first and second sheets or the folding of the first web 12 to sandwich the elastic material can be omitted. In other suitable embodiments, the first web 12 can be formed from spunbond laminates (SBL), necked bonded laminates (NBL), and spunbond-meltblown-spunbond (SMS) nonwovens, which are also suitable materials for use as leg elastics in absorbent articles.

In one suitable embodiment, the base web 14 comprises a material suitable for use as an outer cover of absorbent articles. As one example, the outer cover material may be a multi-layered laminate structure to provide desired levels of extensibility as well as liquid impermeability and vapor permeability. For example, the outer cover may be a two-layer construction, including an outer layer constructed of a vapor permeable material and an inner layer constructed of a liquid impermeable material, with the two layers being secured together by a suitable adhesive. It is understood, however, that the outer cover material can have more or fewer layers (e.g., a single layer plastic film).

In another embodiment, the base web 14 can comprise a material suitable for use as a bodyside liner of absorbent articles. The bodyside liner material can be a material that is suitably pliable, soft feeling, and nonirritating to the wearer's skin. The bodyside liner material should be sufficiently porous to be liquid permeable to thereby permit liquid (e.g., urine) to readily penetrate through its thickness. Suitable bodyside liner materials can be manufactured from a wide selection of web materials.

In use, the base web 14 can be provided from a roll (or other suitable web source) and advanced to the nip 20. In one suitable embodiment, the base web 14 is traveling at a high line speed. As used herein, high line speed refers to a line speed greater than about 600 feet per minute. In some embodiments, the line speed can be greater than about 800 feet per minute, or greater than about 1000 feet per minute. If adhesive unit 76 is configured to apply adhesive 77 to the base web 14 for bonding with the first web 12, the adhesive 77 can be applied onto the base web 14 in the desired nonlinear pattern of adhesive (e.g., a curved pattern) such that the first web 12 can be guided in such a nonlinear pattern. In on such embodiment, the adhesive 77 could be applied to the base web 14 in a nonlinear pattern using a rotary valve, as taught by International Patent Application PCT/US15/52919 of Kimberly Clark Worldwide, Inc. As noted above, the base web 14 can be traveling in the machine direction 24 at a high line speed. The base web 14 can be fed to the nip 20 defined by the back-up roller 22 and the guide roller 16.

As illustrated in FIG. 1, the first web 12 can be fed by a source of the first web 12 (such as a roll). The apparatus 10 guides and applies the first web 12 to the base web 14 in a desired nonlinear pattern 84. In one embodiment, the first web 12 can be fed to an idler roller 78 and then turn 90° downward towards the guide roller 16. The first web 12 can approach the idler roller 78 in a cross direction 26 as illustrated in FIG. 1, however, it is contemplated that the first web 12 can approach the idler roller 78 in other orientations.

Preferably, the first web 12 can be fed over an idler roller 78 and to guide roller 16 under tension which causes the first web 12 to stretch. In one suitable embodiment, the first web 12 is under tension of about 0.1 pound to about 1 pound per linear inch of the first web 12. It is understood, however, that the tension force applied to first web 12 can be different than disclosed herein.

The guide roller 16 is spaced from the idler roller 78 by a vertical distance. The vertical distance can be selected to facilitate proper alignment of the first web 12 as it is fed to the guide roller 16 and to inhibit twisting or bunching of the first web 12 during movement of the guide roller 16 relative to the back-up roller 22. In one suitable configuration, the vertical distance between the guide roller 16 and the idler roller 78 is approximately 10 times the width of the first web 12.

In the illustrated embodiment, the first web 12 is wrapped around approximately 90 degrees of the circumference of each of the idler roller 78 and the guide roller 16. In other words, the first web 12 extends around about a quarter of the circumference of the rollers 78, 16 as it passes over the respective roller. It is understood that the first web 12 can be wrapped around more or less of the circumference of one or more of the rollers 78, 16 by changing the angle at which the first web 12 is fed to the respective roller (i.e., the approach angle of the first web 12).

The guide roller translation system 18 can move the cross-directional position Y (as labeled in FIG. 2) of the guide roller 16 that guides the first web 12 to the base web 14. The guide roller translation system 18 can also pivot the guide roller 16 with respect to the back-up roller 22 such that the guide roller rotational axis 28 can define the lead angle θ with respect to the back-up roller rotational axis 30, as described above and as illustrated in FIG. 2. Thus, the guide roller translation system 18 can guide the first web 12 in a nonlinear pattern 84 with respect to the base web 14.

The apparatus 10 is adapted to apply the first web 12 to the base web 14 with significant curvature while the base web 14 is traveling at high line speeds. As used herein, "significant curvature" refers to the acute angle α defined by a line tangent to the elastic curve and the longitudinal centerline of the web that is greater than about 45 degrees (see FIG. 13). It is conceived that the nonlinear pattern 84 of the first web 12 on the base web 14 can have curved segment 85 be a mirror image of curved segment 87. It is also conceived that the nonlinear pattern 84 of the first web 12 on the base web 14 can be configured such that the generally curved segment 85 can have a different curvature or acute angle α than the generally curved segment 87.

Figure 7:
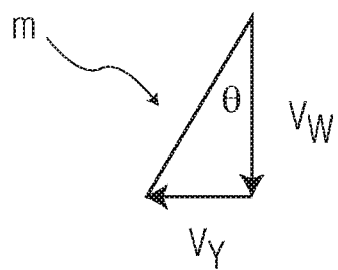
FIG. 7 illustrates a diagram for calculating the slope of the first web with respect to the back-up roller rotational axis as the first web meets the base web in the nip.

When the guide roller rotational axis 28 is parallel to the back-up roller rotational axis 30 (i.e., the lead angle θ is 0°), the guide roller 16 remains in a constant cross directional position Y and guides the first web 12 into the nip 20 and to the base web 14 at a constant cross direction location. However, when the lead angle θ is anything other than 0°, the guide roller 16 will translate in the cross direction 26 along the back-up roller rotational axis 30, changing the cross direction position Y of the guide roller 16, and thus, the cross direction position of the nip 20. In doing so, a cross direction position Y of the guide roller 16 with respect to the back-up roller 22 can change as the cross direction cable 40 either winds or unwinds from the cross direction windlass 36 and the cross direction pulley 38. When the cross direction cable 40 either winds or unwinds from the cross direction windlass 36 and the cross direction pulley 38, the guide block 44 can slidably move on the guide rods 42. As such, the guide roller 16 can guide the first web 12 with respect to the base web 14 in the cross direction 26, as well as change the incoming angle of the first web 12 with respect to the base web 14 (which is equal to the lead angle θ). The lead angle θ is equal to the trigonometric arctangent of the slope m of the first web 12 on the base web 14, as labeled in FIG. 2 and demonstrated in FIG. 7, represented by the velocity $V_Y$ of the guide roller 16 in the cross direction 26 and the velocity $V_X$ of the base web 14 in the machine direction 24. The lead angle θ can change as the angular cable 52 either winds or unwinds from the angular windlass 46, the angular pulley 48 and the guide windlass 50. Traction between the guide roller 16 and the back-up roller 22 combined with the lead angle θ can drive the guide roller 16 in the cross direction 26. As discussed above, in one embodiment this cross direction 26 movement of the guide roller 16 can be accomplished through the guide block 44 moving along the guide rods 42 by the guide roller translation system 18.

The placement of the first web 12 onto the base web 14 can be controlled by the apparatus 10 as illustrated in FIGS. 1-6 and as discussed above, however, since there may be slippage or imperfect contact between the roller 54 of guide roller 16 and the back-up roller 22, a motor or cambox can be employed as part of the cross direction funicular mechanism 32 of the guide roller translation system 18 to ensure that the cross direction position Y of the guide roller 16 remains synchronized with the machine direction advancement of the base web 14 to provide the desired nonlinear pattern 84 of the first web 12 on the base web 14. In some embodiments, a second motor or cambox can be employed as part of the angular funicular mechanism 34 of the guide roller translation system 18 to ensure the proper lead angle θ of the guide roller 16 is achieved.

Figure 8:
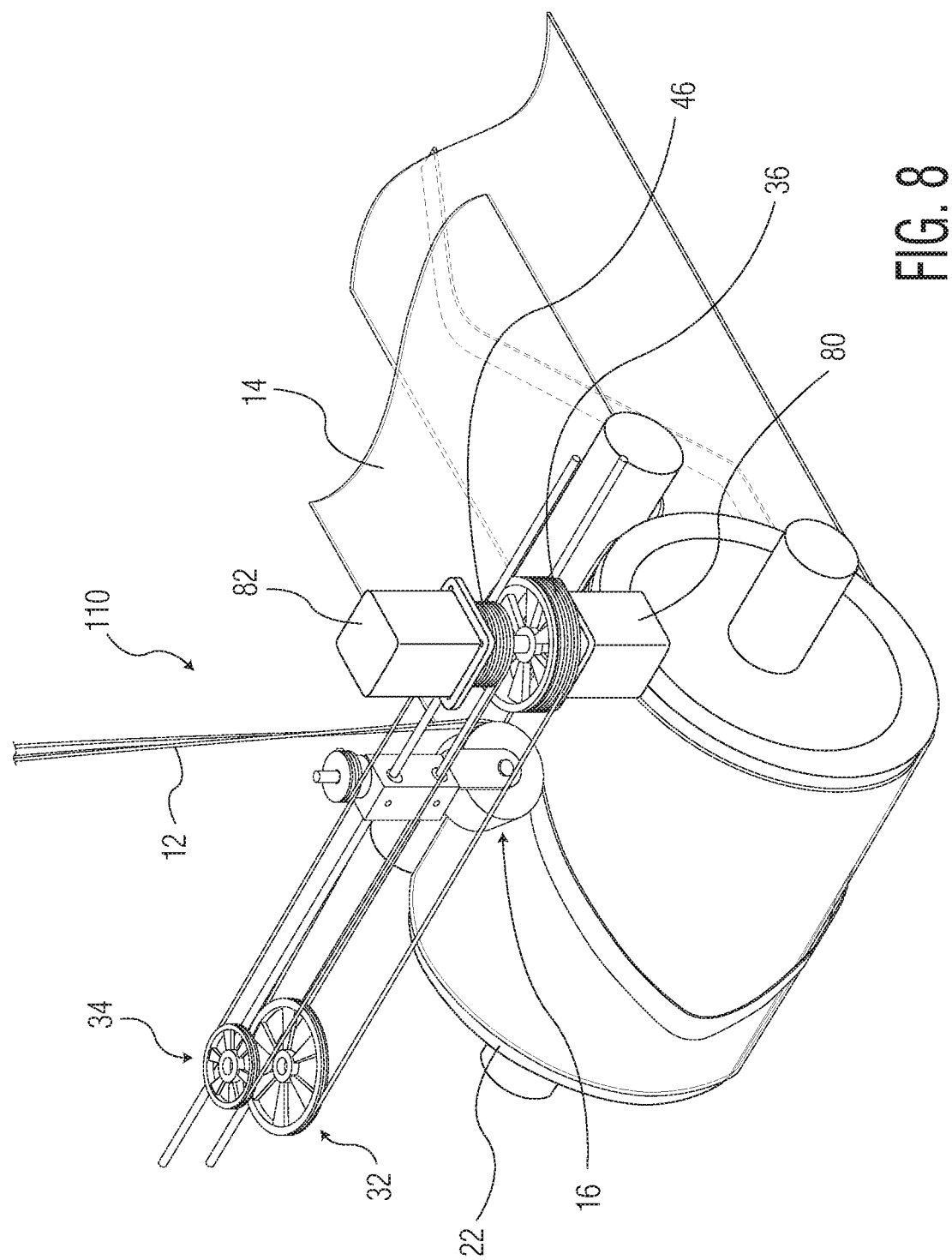
FIG. 8 illustrates a top, front perspective view of a second embodiment of an apparatus for applying a first web to a base web in a nonlinear pattern.

For example, FIG. 8 illustrates an embodiment of an apparatus 110 that includes a cross direction motor 80 that forms part of the cross direction funicular mechanism 32 and an angular motor 82 that forms part of the angular funicular mechanism 34 of the guide roller translation system 18. Unless otherwise noted, the components and operation of the apparatus 110 are the same as for apparatus 10 illustrated in FIGS. 1-6 and discussed above. The cross direction motor 80 includes an output shaft (not shown) that can be coupled to the cross direction windlass 36. The angular motor 82 includes an output shaft (not shown) that can be coupled to the angular windlass 46. In a preferred embodiment, the cross direction motor 80 and the angular motor 82 are servo motors. However, it is contemplated that the cross direction motor 80 and/or the angular motor 82 can be any other suitable type of motor or drive for controlling the rotation of the cross direction windlass 36 and the angular windlass 46, respectively.

The desired lead angle θ of the guide roller 16 can be a function of both the cross direction position of the guide block 44 and the angular windlass 46. As an example, to hold the guide roller 16 at a fixed, non-zero, lead angle θ, the contact of the roller 54 with back-up roller 22 would tend to desire to drive the guide roller 16 in a cross direction 26. If while the guide roller 16 moved in such a cross direction 26 the angular windlass 46 was held in a fixed position, then the angular cable 52 wrapping the guide windlass 50 would cause the guide windlass 50 to rotate changing the lead angle θ. Therefore, to keep the lead angle θ at a fixed angle, the angular windlass 46 needs to advance the angular cable 52 (by either winding or unwinding the angular cable 52 from the angular windlass 46) in an amount equal to the cross direction 26 movement of the guide roller 16. In other words, for every cross direction increment of movement of the guide roller 16, the angular cable 52 must move that same amount and in the same direction in order to maintain the guide roller 16 at a fixed lead angle θ. If one wished to change the lead angle θ (either increasing or decreasing), the angular windlass 46 still needs to somewhat closely match the cross direction 26 motion of the guide roller 16, but either slightly increase or slightly decrease the movement of the angular cable 52 in comparison to the cross direction 26 movement of the guide roller 16 in order to change the lead angle θ in a controlled fashion.

A cam table for a servo motor or mechanical cam can be prepared by creating a table of X-Y coordinates of points that define a desired pattern 84 (as labeled in FIGS. 2 and 13) of the first web 12 on the base web 14 with X points running in the machine direction 24 and Y points running in the cross direction 26. The desired pattern 84 repeat length should be divided into a specified amount N of equally spaced increments. The required lead angle θ at each point along the elastic path can be determined from the formula (1):

$$\theta_n = \text{Atan}\left(\frac{y_{n+1} - y_n}{x_{n+1} - x_n}\right) \quad (1)$$

The corresponding angle φ of the angular windlass 46 and the corresponding angle ß of the cross direction windlass 36 (as labeled in FIG. 12) can be determined by the respective formulas (2) and (3) below:

$$\phi_n = \frac{R_g}{R_A}\theta_n + \frac{1}{R_A}y_n \quad (2)$$

$$\beta_n = \frac{1}{R_{CD}}y_n \quad (3)$$

For formulas (1), (2), and (3), the following variables are defined by Table 1 below:

TABLE 1

Variable and Definitions

| Variable | Definition |
|---|---|
| L | Desired pattern repeat length in machine direction |
| N | Total number of steps into which desired pattern repeat length is divided |
| n | Step count number (i.e., n = 0 to N) |
| $y_n$ | Guide roller position at step n |
| $y_{n-1}$ | Guide roller position at step n − 1 |
| $y_{n+1}$ | Guide roller position at step n + 1 |
| $m_n$ | First web slope at step n |
| $m_{n-1}$ | First web slope at step n − 1 |
| $\theta_n$ | Guide windlass angle, a.k.a. Lead angle, (radians) at step n |
| $\gamma_{SG1}$ | First side gear angle at step n |
| $\gamma_{SG2}$ | Second side gear angle at step n |
| $\gamma_{Spider}$ | Spider gear angle at step n |
| $\phi_n$ | Angular windlass angle at step n |
| $\beta_n$ | Cross direction windlass angle at step n |
| $R_g$ | Radius of guide windlass |
| $R_A$ | Radius of angular windlass |
| $R_{CD}$ | Radius of cross direction windlass |

Figure 9:
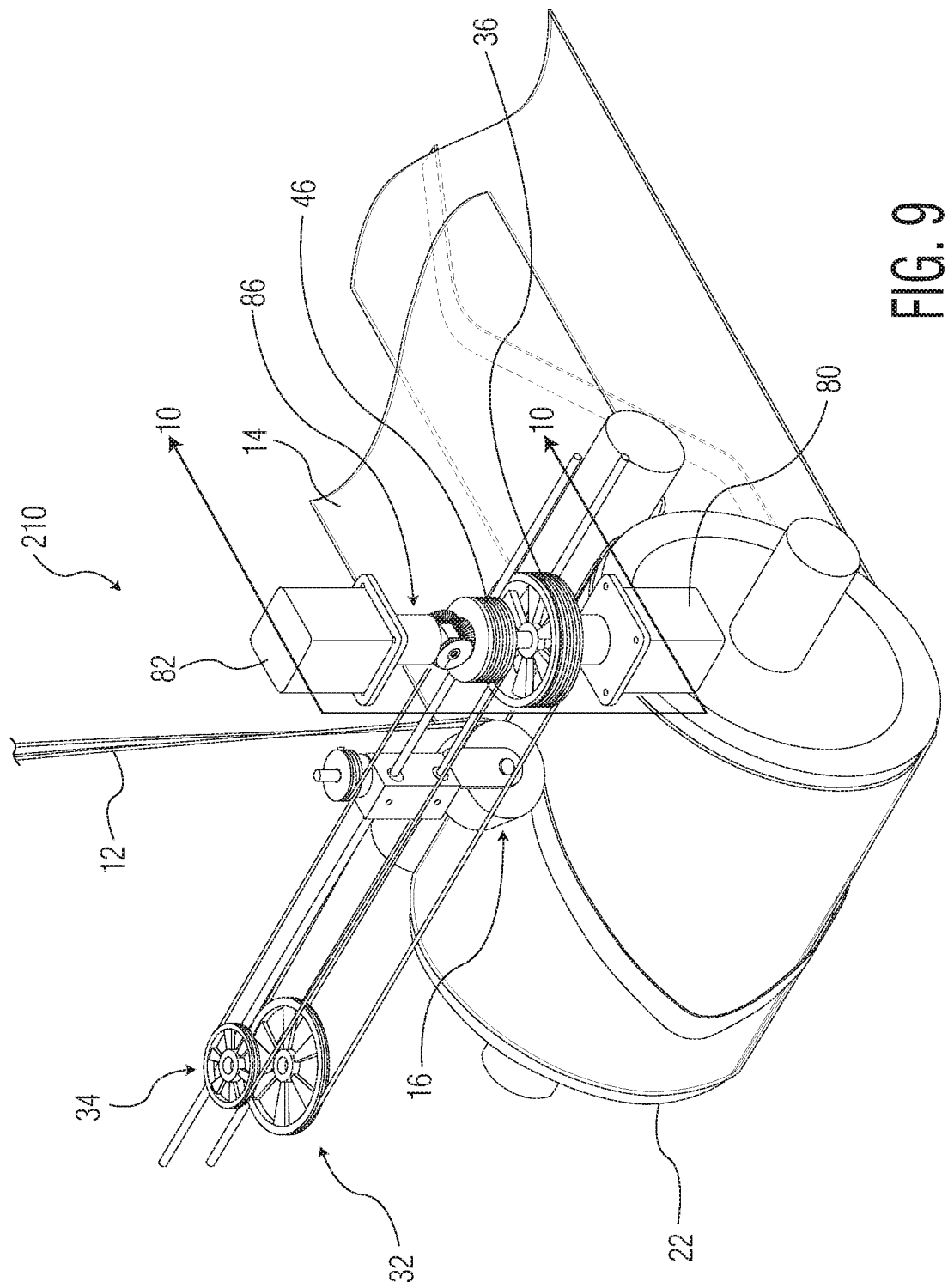
FIG. 9 illustrates a top, front perspective view of a third embodiment of an apparatus for applying a first web to a base web in a nonlinear pattern.
Figure 12:
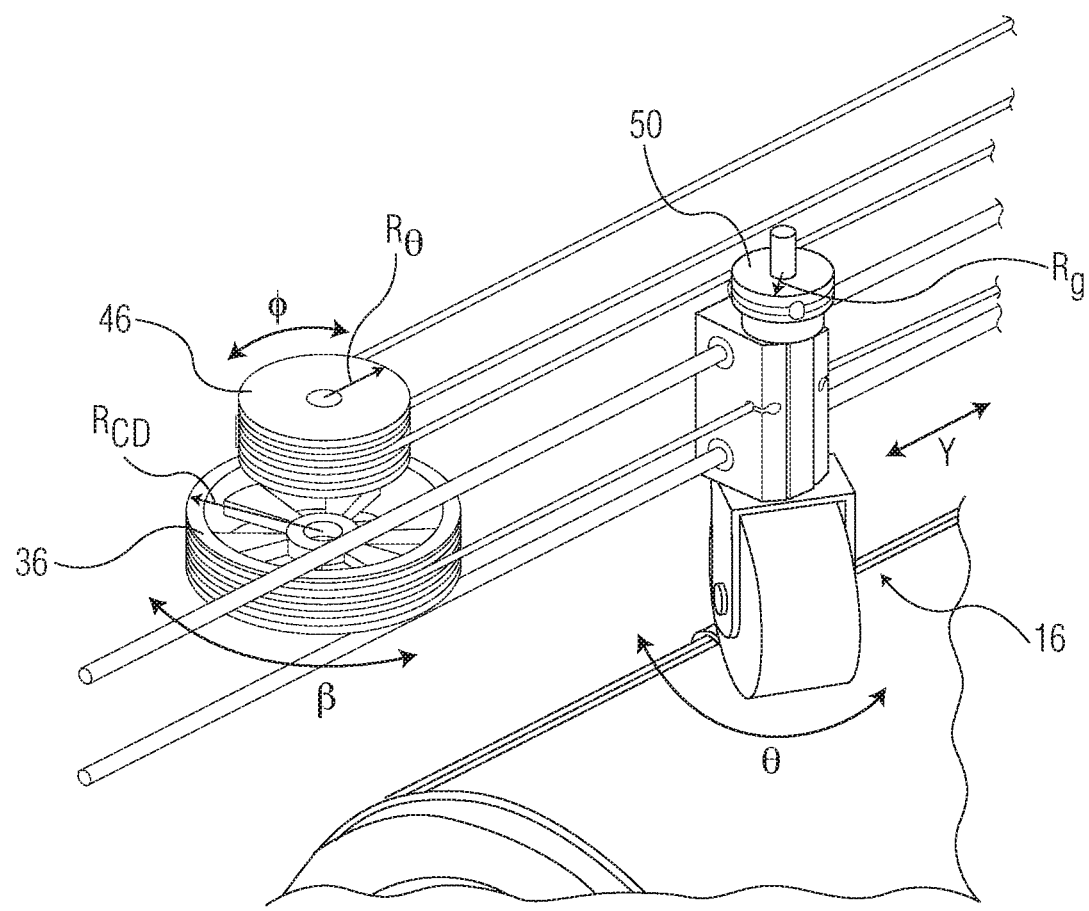
FIG. 12 illustrates a top, rear perspective view of some of the components of the guide translation system of the embodiment depicted in FIG. 9 with the motors removed for clarity.

FIG. 9 illustrates yet another embodiment of an apparatus 210 for guiding and applying first web 12 to the guide web 14. Again, unless otherwise noted, the components and operation of the apparatus 210 are the same as for apparatus 10 illustrated in FIGS. 1-6 and apparatus 110 illustrated in FIG. 8 and discussed above. The apparatus 210 includes a differential 86 that can be utilized along with proper selection of the radius $R_{CD}$ of the cross direction windlass 36 and the radius $R_\theta$ of the angular windlass 46 to perform the mathematical functions of the equations (2) and (3) above such that the angular motor 82 only needs to be programmed with the desired values of lead angle θ at each increment (n) on the desired pattern length (L). FIG. 12 illustrates the radius $R_{CD}$ of the cross direction windlass 36, the radius $R_\theta$ of the angular windlass 46, and the radius $R_g$ of the guide windlass 50, with the motors 80, 82 and differential 86 being removed for clarity purposes.

Figure 10:
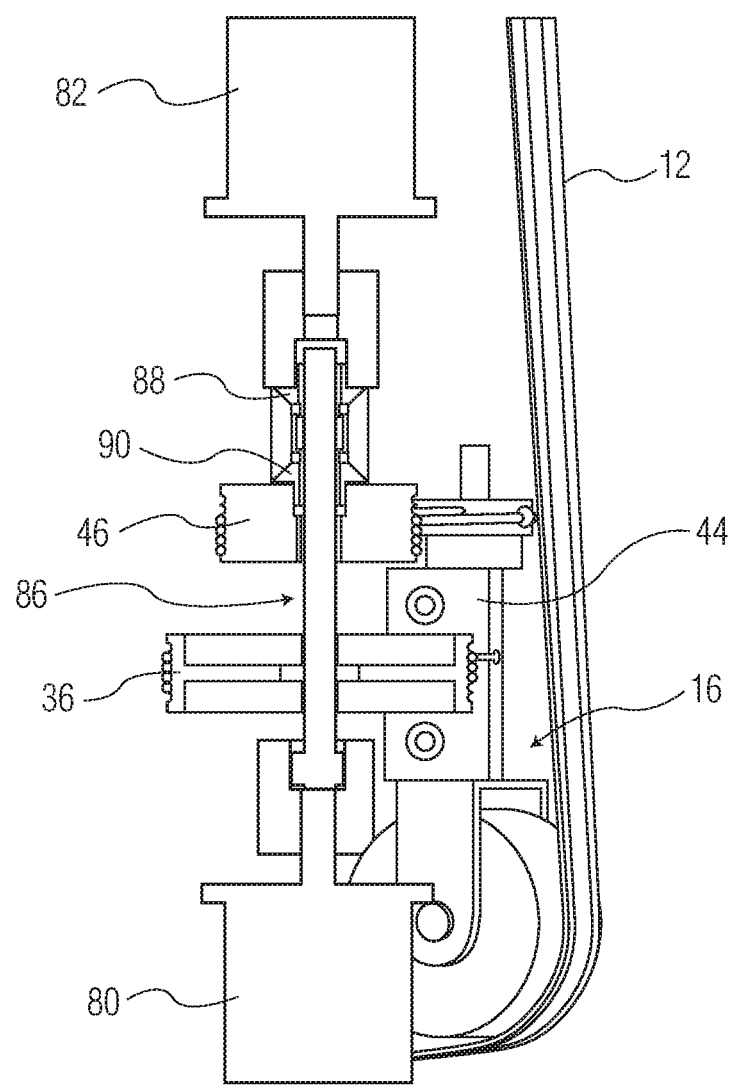
FIG. 10 illustrates a cross-sectional view of select components of the guide translation system taken along line 10-10 in FIG. 9.
Figure 11:
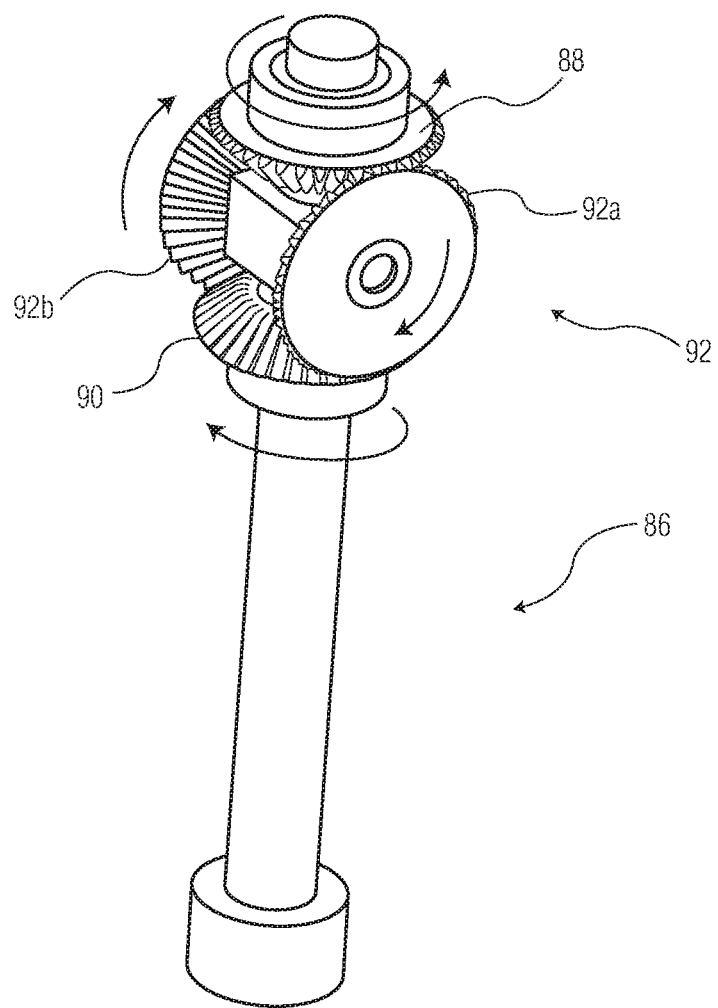
FIG. 11 illustrates a perspective view of an exemplary differential used in the guide translation system of the embodiment depicted in FIG. 9.

FIG. 10 illustrates a cross sectional view of the apparatus 210 taken along line 10-10 in FIG. 9 and FIG. 11 illustrates a perspective view of the differential 86 of apparatus 210. As illustrated in FIGS. 10 and 11, the differential 86 can include a first side gear 88, a second side gear 90, and a spider gear 92. The spider gear 92 can include a first component 92a and a second component 92b. The differential 86 can couple the angular windlass 46 to the cross direction windlass 36 such that the rotation of the cross direction windlass 36 is timed with the rotation of the angular windlass 46. The differential 86 can be coupled to the output shaft of the angular motor 82 and can be coupled to the output shaft of the cross direction motor 80. The speed relationship between the side gears 88, 90 in the differential 86 can be defined by equation (4) below:

$$\omega_{spider} = \tfrac{1}{2}(\omega_{side\ gear\ \#2} - \omega_{side\ gear\ \#1}) \quad (4)$$

If the angular velocities in equation (4) above are integrated over the same interval of time, the velocities can be replaced with the angular movement of each side gear 88, 90 and equation (4) can be rewritten to define the relationship of the angles of the side gears 88, 90 in equation (5) below:

$$\gamma_{SG2} = \gamma_{SG1} + 2\gamma_{Spider} \quad (5)$$

The angle of the second side gear 90 establishes the desired lead angle θ when scaled by the ratio of the guide windlass 50 radius $R_g$ to the angular windlass 46 radius $R_\theta$ as shown by equation (6) below:

$$\gamma_{SG2} = \frac{R_g}{R_{CD}}\theta_n \quad (6)$$

The angle of the first side gear 88 is the same as the angular windlass 46 angle φ as shown by equation (7) below:

$$\gamma_{SG1} = \phi_n \quad (7)$$

The angle of the spider gear 92 is the same as the cross direction windlass 36 angle ß as shown by equation (8) below:

$$\gamma_{Spider} = \beta_n = \frac{1}{R_Y}y_n \quad (8)$$

Substituting equations (6) and (8) into equation (5), it is demonstrated that equation (5) will be the same as equation (2) as long as the ratio of the cross direction windlass 36 radius $R_{CD}$ to the angular windlass 46 radius $R_\theta$ is 2:1, as shown by equation (9) below:

$$\frac{R_{CD}}{R_\theta} = 2 \quad (9)$$

The apparatuses 10, 110, 210 described herein can provide several benefits in guiding and applying the first web 12 to the base web 14 in a nonlinear pattern 84. First, by locating the control of the cross direction 26 position and the lead angle θ of the first web 12 with respect to the base web 14 at the location of the nip 20, less motion of the guide roller 16 is required in areas where the slope m of the first web 12 is high or is changing rapidly to provide the desired nonlinear pattern 84. When a first web 12, such as an elastic web, is guided into a nip 20 using a guide placed a distance from the nip 20, there is always over-travel of the guide compared to the desired pattern and the amount of the over-travel increases as the distance to the nip 20 increases. By locating the control of the cross-direction 26 position and the lead angle θ of the first web 12 with respect to the base web 14 at the location of the nip 20, there is no such over-travel, as the guide roller 16 motion matches the desired pattern 84 of the first web 12 on the base web 14.

Second, such a reduction in movement of the guide roller 16 in areas where the slope m of the first web 12 is high or changing rapidly reduces strain on the first web 12. This can lead to reducing the possibility that the first web 12 breaks under tension, and thus, can lead to an increase in machine line efficiency as compared to systems where the guiding of the first web 12 is controlled at a distance away from the nip 20, which require more exaggerated movements of the guiding system.

Figure 13:
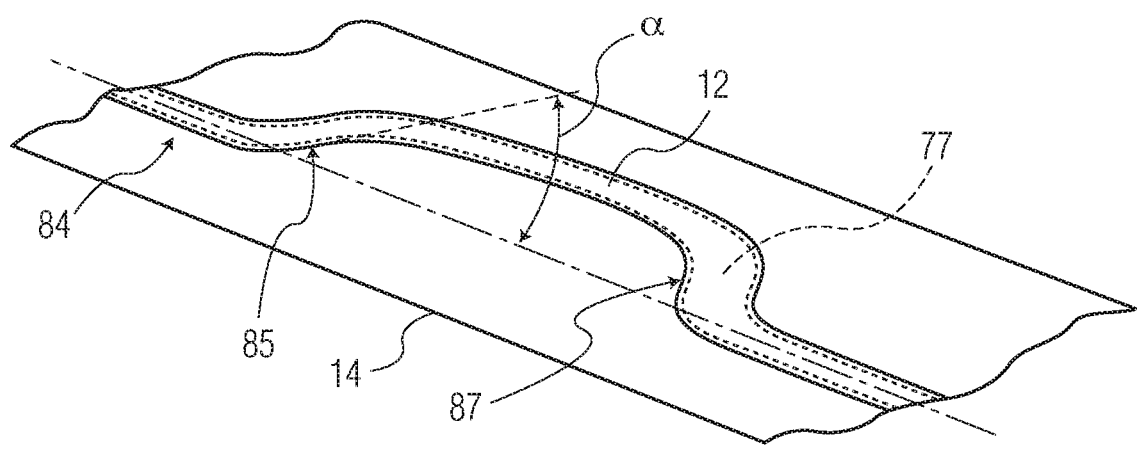
FIG. 13 illustrates a perspective view of a portion of a base web showing the first web adhered thereto in a nonlinear pattern.

One suitable embodiment of the resulting composite (i.e., the base web 14 having the first web 12 adhered thereto by adhesive 77) is illustrated in FIG. 13. The composite can be used in the manufacture of absorbent articles (e.g., diapers, training pants, inconstancy articles). In one particularly suitable configuration, the base web 14 can be used to form outer covers of absorbent articles and the first web 12 can be used to form leg elastics of the absorbent articles. One such absorbent article is illustrated in FIG. 14 in the form of an incontinence garment 300.

Figure 14:
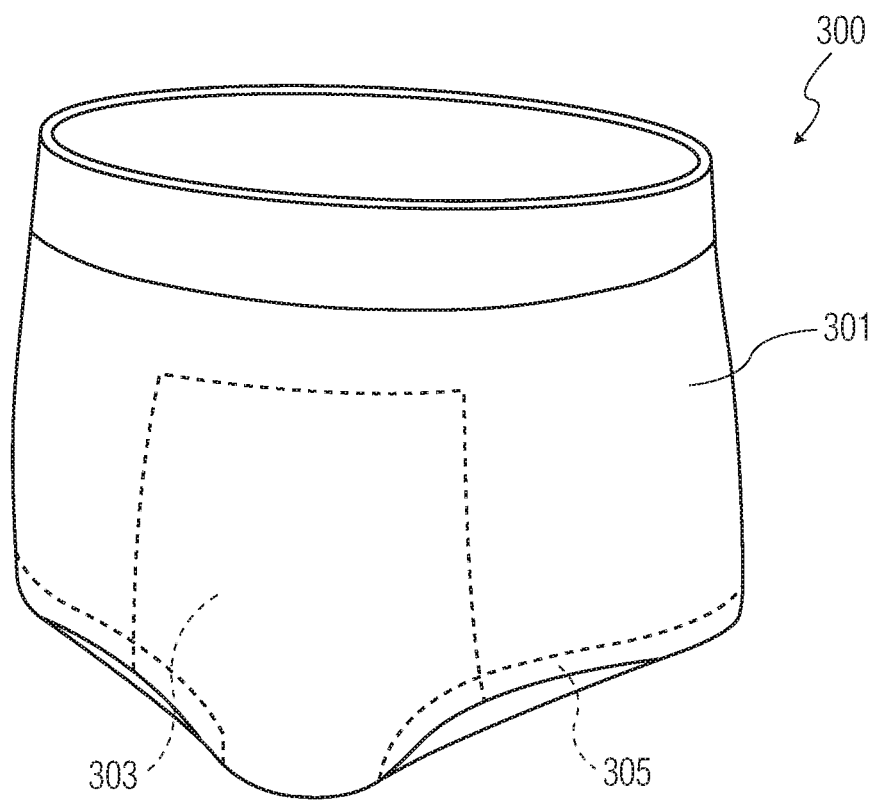
FIG. 14 illustrates a perspective view of one embodiment of an absorbent article in the form of an incontinence garment.

As seen in FIG. 14, the incontinence garment 300 comprises an outer cover 301, an absorbent core 303, and leg elastics 305. The outer cover 301 can be made from the base web 14 and the leg elastics 305 can be defined by the first web 12. It is understood that the garment 300 can include numerous other components (e.g., a bodyside liner, fasteners) other than those illustrated and described herein.

EMBODIMENTS

Embodiment 1: An apparatus for applying a first web to a base web in a nonlinear pattern as the base web is advanced in a machine direction in contact with a back-up roller, the apparatus comprising: a guide roller; and a guide roller translation system; wherein the guide roller is configured to define a nip with the back-up roller, the guide roller translation system being configured to allow the guide roller to move with respect to the back-up roller to control the position of the nip to allow the first web to be applied to the base web in the non-linear pattern in the machine direction.
Embodiment 2: The apparatus of embodiment 1, wherein the guide roller is configured to move with respect to the back-up roller in a cross direction.
Embodiment 3: The apparatus of embodiment 1 or 2, wherein the guide roller comprises a guide roller rotational axis and the back-up roller comprises a back-up roller rotational axis, and wherein the guide roller rotational axis can pivot with respect to the back-up roller rotational axis such that the guide roller rotational axis defines a lead angle with the back-up roller rotational axis.
Embodiment 4: The apparatus of embodiment 3, wherein the guide roller translation system comprises: a cross direction windlass; a cross direction pulley; a cross direction cable, the cross direction cable configured to be wound and unwound on the cross direction windlass and the cross direction pulley; at least one guide rod; and a guide block, the guide block supporting the guide roller and the guide block being slidably mounted to the at least one guide rod and being mounted to the cross direction cable such that as the cross direction cable is wound and unwound on the cross direction windlass and the cross direction pulley the guide block can slide on the at least one guide rod.
Embodiment 5: The apparatus of embodiment 4, wherein the guide roller translation system further comprises: an angular windlass; an angular pulley; a guide windlass; and an angular cable, the angular cable configured to be wound and unwound on the angular windlass, the angular pulley, and the guide windlass.
Embodiment 6: The apparatus of embodiment 4, wherein a cross direction position of the guide roller with respect to the back-up roller changes as the cross direction cable winds and unwinds from the cross direction windlass and the cross direction pulley.
Embodiment 7: The apparatus of embodiment 5, wherein the lead angle changes as the angular cable winds and unwinds from the angular windlass, the angular pulley, and the guide windlass.
Embodiment 8: The apparatus of embodiment 5, wherein the guide roller translation system further comprises: a first motor including a first output shaft, the first output shaft being coupled to the cross direction windlass.
Embodiment 9: The apparatus of embodiment 8, wherein the guide roller translation system further comprises: a second motor including a second output shaft, the second output shaft being coupled to the angular windlass.
Embodiment 10: The apparatus of embodiment 9, wherein the guide roller translation system further comprises: a differential coupled to the first output shaft and the second output shaft such that the rotation of the cross direction windlass is timed with the rotation of the angular windlass.
Embodiment 11: The apparatus of any one of the preceding embodiments, further comprising an adhesive unit, the adhesive unit applying adhesive to at least one of the first web and the base web prior to the first web and the base web entering the nip such that the first web bonds to the base web at the nip.
Embodiment 12: The apparatus of any one of the preceding embodiments, wherein the first web is elastic.
Embodiment 13: A method for applying a first web to a base web in a nonlinear pattern, the method comprising: providing the first web; providing the base web; advancing the base web in a machine direction; advancing the first web in the machine direction; providing a nip for applying the first web and the base web, the nip being defined by a back-up roller and a guide roller, the first web being engaged by the guide roller; controlling a cross direction position of the first web in relation to the base web by adjusting a position of the guide roller with respect to the back-up roller to allow the first web to be applied to the base web in the non-linear pattern in the machine direction.
Embodiment 14: The method of embodiment 13, wherein adjusting the position of the guide roller with respect to the back-up roller includes moving the guide roller with respect to the back-up roller in a cross direction.
Embodiment 15: The method of embodiment 13 or embodiment 14, wherein the guide roller comprises a guide roller rotational axis and the back-up roller comprises a back-up roller rotational axis, and wherein adjusting the position of the guide roller with respect to the back-up roller includes pivoting the guide roller with respect to the back-up roller such that the guide roller rotational axis defines a lead angle with the back-up roller rotational axis.

Embodiment 16: The method of embodiment 15, further comprising providing a guide roller translation system, the guide roller translation system comprising: a cross direction windlass; a cross direction pulley; a cross direction cable, the cross direction cable configured to be wound and unwound on the cross direction windlass and the cross direction pulley; at least one guide rod; and a guide block, the guide block supporting the guide roller and the guide block being slidably mounted to the at least one guide rod and being mounted to the cross direction cable such that as the cross direction cable is wound and unwound on the cross direction windlass and the cross direction pulley the guide block can slide on the at least one guide rod.

Embodiment 17: The method of embodiment 16, wherein the guide roller translation system further comprises: an angular windlass; an angular pulley; a guide windlass; and an angular cable, the angular cable configured to be wound and unwound on the angular windlass, the angular pulley, and the guide windlass.

Embodiment 18: The method of embodiment 16, wherein a cross direction position of the guide roller with respect to the back-up roller changes as the cross direction cable winds and unwinds from the cross direction windlass and the cross direction pulley.

Embodiment 19: The method of embodiment 17, wherein the lead angle changes as the angular cable winds and unwinds from the angular windlass, the angular pulley, and the guide windlass.

Embodiment 20: The method of any one of embodiments 13-19, further comprising: bonding the first web to the base web at the nip.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. An apparatus for applying a first web to a base web in a nonlinear pattern as the base web is advanced in a machine direction in contact with a back-up roller, the apparatus comprising:
   a guide roller; and
   a guide roller translation system;
   wherein the guide roller comprises a guide roller rotational axis and the back-up roller comprises a back-up roller rotational axis;
   wherein the guide roller rotational axis extends in a cross direction perpendicular to the machine direction;
   wherein the guide roller is configured to define a nip with the back-up roller, the guide roller translation system being configured to allow the guide roller to move with respect to the back-up roller to control a position of the nip to allow the first web to be applied to the base web in the non-linear pattern in the machine direction, and
   wherein the guide roller translation system includes a cross direction funicular mechanism configured to allow the guide roller to move cross directionally with respect to the back-up roller and an angular funicular mechanism configured to allow the guide roller to pivot with response to the back-up roller around a pivot axis, the pivot axis being perpendicular to both the guide roller rotational axis and the back-up roller rotational axis,
   wherein the guide roller rotational axis can pivot with respect to the back-up roller rotational axis such that the guide roller rotational axis defines a lead angle with the back-up roller rotational axis, and
   wherein the cross direction funicular mechanism comprises:
   a cross direction windlass;
   a cross direction pulley;
   a cross direction cable, the cross direction cable configured to be wound and unwound on the cross direction windlass and the cross direction pulley;
   a guide rod; and
   a guide block, the guide block supporting the guide roller and the guide block being slidably mounted to the guide rod and being mounted to the cross direction cable such that as the cross direction cable is wound and unwound on the cross direction windlass and the cross direction pulley the guide block can slide on the guide rod;
   wherein the angular funicular mechanism comprises:
   an angular windlass;
   an angular pulley;
   a guide windlass coupled to the guide roller and configured to pivot along with the guide roller; and
   an angular cable, the angular cable configured to be wound and unwound on the angular windlass, the angular pulley, and the guide windlass,
   wherein the angular cable is fastened to the angular windlass,
   wherein the angular pulley is movable in the cross direction so as to remove any slack in the angular cable, and
   wherein a rotation of the angular windlass causes the guide windlass to rotate via the angular cable, causing the guide roller to pivot to thereby change the lead angle.

2. The apparatus of claim 1, wherein a cross direction position of the guide roller with respect to the back-up roller changes as the cross direction cable winds and unwinds from the cross direction windlass and the cross direction pulley.

3. The apparatus of claim 1, further comprising an adhesive unit, the adhesive unit applying adhesive to at least one of the first web and the base web prior to the first web and the base web entering the nip such that the first web bonds to the base web at the nip.

4. The apparatus of claim 1, wherein the first web is elastic.

5. A method for applying a first web to a base web in a nonlinear pattern, the method comprising:
   providing the first web;
   providing the base web;
   advancing the base web in a machine direction;
   advancing the first web in the machine direction;
   providing a nip for applying the first web to the base web, the nip being defined by a back-up roller and a guide roller, the first web being engaged by the guide roller, wherein the guide roller comprises a guide roller rotational axis extending in a cross direction perpendicular to the machine direction, and the back-up roller comprises a back-up roller rotational axis;
   controlling a cross direction position of the first web in relation to the base web by adjusting a position of the guide roller with respect to the back-up roller to allow the first web to be applied to the base web in the non-linear pattern in the machine direction,
   and wherein adjusting the position of the guide roller with respect to the back-up roller includes pivoting the guide roller with respect to the back-up roller such that the guide roller rotational axis defines a lead angle with the back-up roller rotational axis, wherein a guide roller translation system includes a cross direction funicular mechanism configured to allow the guide roller to move cross directionally with respect to the back-up roller and an angular funicular mechanism configured to allow the guide roller to pivot with respect to the back-up roller around a pivot axis, the pivot axis being perpendicular to both the guide roller rotational axis and the back-up roller rotational axis, wherein the guide roller rotational axis can pivot with respect to the back-up roller rotational axis such that the guide roller rotational axis defines a lead angle with the back-up roller rotational axis, and wherein the cross direction funicular mechanism comprises:

a cross direction windlass;

a cross direction pulley;

a cross direction cable, the cross direction cable configured to be wound and unwound on the cross direction windlass and the cross direction pulley;

a guide rod; and a guide block, the guide block supporting the guide roller and the guide block being slidably mounted to the guide rod and being mounted to the cross direction cable such that as the cross direction cable is wound and unwound on the cross direction windlass and the cross direction pulley the guide block can slide on the guide rod, wherein the angular funicular mechanism comprises:

an angular windlass;

an angular pulley;

a guide windlass coupled to the guide roller and configured to pivot along with the guide roller; and an angular cable, the angular cable configured to be wound an unwound on the angular windlass, the angular pulley, and the guide windlass, wherein the angular cable is fastened to the angular windlass;

wherein the angular pulley is movable in the cross direction so as to remove any slack in the angular cable; and wherein a rotation of the angular windlass causes the guide windlass to rotate vie the angular cable, causing the guide roller to pivot to thereby change the lead angle.

6. The method of claim 5, wherein a cross direction position of the guide roller with respect to the back-up roller changes as the cross direction cable winds and unwinds from the cross direction windlass and the cross direction pulley.

7. The method of claim 5, further comprising:

bonding the first web to the base web at the nip.

* * * * *